(12) United States Patent
Leach et al.

(10) Patent No.: US 6,559,155 B1
(45) Date of Patent: May 6, 2003

(54) PYRIMIDINONE DERIVATIVES FOR THE TREATMENT OF ATHEROSCLEROSIS

(75) Inventors: Colin Andrew Leach, Sawbridgeworth (GB); Stephen Allan Smith, Bishops Stortford (GB)

(73) Assignee: SmithKline Beecham p.l.c. (GB)

( * ) Notice: Subject to any disclaimer, the term of this patent is extended or adjusted under 35 U.S.C. 154(b) by 0 days.

(21) Appl. No.: 09/763,492

(22) PCT Filed: Aug. 18, 1999

(86) PCT No.: PCT/EP99/06093

§ 371 (c)(1),
(2), (4) Date: Feb. 21, 2001

(87) PCT Pub. No.: WO00/10980

PCT Pub. Date: Mar. 2, 2000

(30) Foreign Application Priority Data

| Aug. 21, 1998 | (GB) | ................................................ | 9818375 |
| Jan. 29, 1999 | (GB) | ................................................ | 9902009 |

(51) Int. Cl.[7] .................... A61K 31/505; C07D 403/06; C07D 403/14

(52) U.S. Cl. ................ 514/274; 540/601; 540/544; 540/553; 540/575; 544/3; 544/54; 544/58.6; 544/63; 544/96; 544/120; 544/123; 544/296; 514/211.15; 514/211.08; 514/217.06; 514/227.8; 514/226.8; 514/235.8; 514/255.05

(58) Field of Search ............. 544/296, 3, 63, 544/123; 514/274, 211.15, 211.08, 217.06, 227.8, 226.8, 235.8, 255.05; 540/601, 575

(56) References Cited

U.S. PATENT DOCUMENTS

| 4,145,546 A | 3/1979 | Brown et al. ............ 544/310 |
| 4,154,834 A | 5/1979 | Brown et al. ............ 544/310 |

FOREIGN PATENT DOCUMENTS

| WO | WO 99/24420 | 5/1999 |

*Primary Examiner*—John M. Ford
(74) *Attorney, Agent, or Firm*—James M. Kanagy; Charles M. Kinzig

(57) ABSTRACT

Pyrimidones of formula (I) are inhibitors of the enzyme $LpPLA_2$ and thereof use in treating inter alia atherosclerosis,

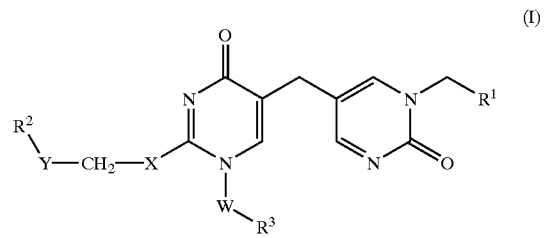

(I)

in which:

$R^1$ is COOH or a salt thereof, $COOR^{10}$, $CONR^{11}R^{12}$, CN or $CH_2OH$;

$R^2$ is a mono- or bicyclic aromatic ring system or a mono- or bicyclic heteroaromatic ring system;

$R^3$ is $C_{1-20}$alkyl, $C_{3-6}$cycloalkyl, $C_{3-6}$cycloalkyl$C_{1-5}$alkyl, $C_{1-10}$alkoxy$C_{1-10}$alkyl, or an aromatic or heteroaromatic ring system;

W is $SO_2$ or a bond;

X is O or S; and

Y is a group of the formula $A^1$—$A^2$—$A^3$ in which $A^1$ and $A^3$ each represent a bond or a straight chain or branched alkylene group, said alkylene group(s) containing a total of 1 to 10 carbon atoms and $A^2$ represents a bond or O, S, SO, $SO_2$, CO, C=$CH_2$, CONH, NHCO, $CR^{15}R^{16}$, CH=CH or C≡C, providing that when $A^2$ is O, S, SO, $SO_2$ or CONH, $A^3$ contains at least two carbon atoms linking the $A^2$ group and the $CH_2$ group in formula (I).

10 Claims, No Drawings

PYRIMIDINONE DERIVATIVES FOR THE TREATMENT OF ATHEROSCLEROSIS

This is a 371 of International Application PCT/EP99/06093, filed Aug. 18, 1999.

The present invention relates to certain novel pyrimidinone compounds, processes for their preparation, intermediates useful in their preparation, pharmaceutical compositions containing them and their use in therapy, in particular in the treatment of atherosclerosis.

WO 95/00649 (SmithKline Beecham plc) describe the phospholipase A2 enzyme Lipoprotein Associated Phospholipase $A_2$ (Lp-$PLA_2$), the sequence, isolation and purification thereof, isolated nucleic acids encoding the enzyme, and recombinant host cells transformed with DNA encoding the enzyme. Suggested therapeutic uses for inhibitors of the enzyme included atherosclerosis, diabetes, rheumatoid arthritis, stroke, myocardial infarction, reperfusion injury and acute and chronic inflammation. A subsequent publication from the same group further describes this enzyme (Tew D et al, Arterioscier Thromb Vas Biol 1996: 16;591–9) wherein it is referred to as LDL-$PLA_2$. A later patent application (WO 95/09921, Icos Corporation) and a related publication in Nature (Tjoelker et al, vol 374, Apr. 6, 1995, 549) describe the enzyme PAF-AH which has essentially the same sequence as Lp-$PLA_2$ and suggest that it may have potential as a therapeutic protein for regulating pathological inflammatory events.

It has been shown that Lp-$PLA_2$ is responsible for the conversion of phosphatidylcholine to lysophosphatidylcholine, during the conversion of low density lipoprotein (LDL) to its oxidised form. The enzyme is known to hydrolyse the sn-2 ester of the oxidised phosphatidylcholine to give lysophosphatidylcholine and an oxidatively modified fatty acid. Both products of Lp-$PLA_2$ action are biologically active with lysophosphatidylcholine, a component of oxidised LDL, known to be a potent chemoattractant for circulating monocytes. As such, lysophosphatidylcholine is thought play a significant role in atherosclerosis by being responsible for the accumulation of cells loaded with cholesterol ester in the arteries. Inhibition of the Lp-$PLA_2$ enzyme would therefore be expected to stop the build up of these macrophage enriched lesions (by inhibition of the formation of lysophosphatidylcholine and oxidised free fatty acids) and so be useful in the treatment of atherosclerosis.

The increased lysophosphatidylcholine content of oxidatively modified LDL is also thought to be responsible for the endothelial dysfunction observed in patients with atherosclerosis. Inhibitors of Lp-$PLA_2$ could therefore prove beneficial in the treatment of this phenomenon. An Lp-$PLA_2$ inhibitor could also find utility in other disease states that exhibit endothelial dysfunction including diabetes, hypertension, angina pectoris and after ischaemia and reperfusion.

In addition, Lp-$PLA_2$ inhibitors may also have a general application in any disorder that involves activated monocytes, macrophages or lymphocytes, as all of these cell types express Lp-$PLA_2$. Examples of such disorders include psoriasis.

Furthermore, Lp-$PLA_2$ inhibitors may also have a general application in any disorder that involves lipid peroxidation in conjunction with Lp-$PLA_2$ activity to produce the two injurious products, lysophosphatidylcholine and oxidatively modified fatty acids. Such conditions include the aforementioned conditions atherosclerosis, diabetes, rheumatoid arthritis, stroke, myocardial infarction, reperfusion injury and acute and chronic inflammation. Further such conditions include various neuropsychiatric disorders such as schizophrenia (see Psychopharmacology Bulletin, 31, 159–165, 1995).

Patent applications WO 96/12963, WO 96/13484, WO96/19451, WO 97/02242, WO97/217675, WO97/217676, WO 96/41098, and WO97/41099 (SmithKline Beecham plc) disclose inter alia various series of 4-thionyl/sulfinyl/sulfonyl azetidinone compounds which are inhibitors of the enzyme Lp-$PLA_2$. These are irreversible, acylating inhibitors (Tew et al, Biochemistry, 37, 10087, 1998).

WO 99/24420 (SmithKline Beecham) describes a new class of compounds which are inhibitors of Lp-$PLA_2$, namely a group of pyrimidone compounds. We have now identified a particular subset of pyrimidone compounds which have a 5-(2-oxopyrimid-5-ylmethyl) substituent and which are potent inhibitors of Lp-$PLA_2$ Accordingly, the present invention provides a compound of the formula (I):

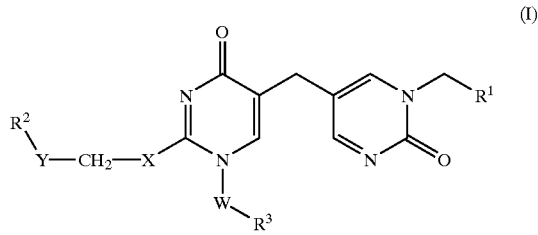

in which:

$R^1$ is COOH or a salt thereof, $COOR^{10}$, $CONR^{11}R^{12}$, CN or $CH_2OH$;

$R^2$ is a mono- or bicyclic aromatic ring system containing up to 10 carbon atoms in the ring system, or a mono- or bicyclic heteroaromatic ring system including up to 4 heteroatoms selected from N, O and S; optionally substituted by 1, 2, 3 or 4 substituents selected from $C_{1-4}$alkyl, $C_{1-4}$alkoxy, $C_{1-4}$alkylthio, aryl, aralkyl, hydroxy, oxo, halogen, CN, COOH or a salt thereof, COO—$C_{1-6}$alkyl, $CONR^{15}R^{16}$, $NR^{15}COR^{16}$, $SO_2NR^{15}R^{16}$, $NR^{15}SO_2R^{16}$, $NR^{15}R^{16}$, mono to perfluoro $C_{1-4}$alkyl and mono to perfluoro $C_{1-4}$alkoxy;

$R^3$ is $C_{1-20}$ alkyl, $C_{3-6}$ cycloalkyl, $C_{3-6}$cycloalkyl$C_{1-5}$alkyl, or $C_{1-10}$ alkoxy$C_{1-10}$alkyl, each optionally substituted by 1 or 2 substituents selected from hydroxy, $C_{1-10}$ alkoxy, COOH or a salt thereof, $COOC_{1-15}$ alkyl, $CONR^{17}R^{18}$, $NR^{17}R^{18}$, $NR^{17}COR^{18}$, $NR^{19}$ or an aromatic or heteroaromatic ring system as defined for $R^2$, or $R^3$ is an aromatic or heteroaromatic ring system as hereinbefore defined for $R^2$;

$R^{10}$ is $C_{1-4}$alkyl or a pharmaceutically acceptable in vivo hydrolysable ester group;

$R^{11}$ and $R^{12}$ which may be the same or different is each selected from hydrogen, $C_{1-12}$alkyl, $CH_2R^{13}$, $CHR^{14}CO_2H$ or a salt thereof, or $R^{11}$ and $R^{12}$ together with the nitrogen to which they are attached form a 5- to 7 membered ring optionally containing one or more further heteroatoms selected from oxygen, nitrogen and sulphur, and optionally substituted by one or two substituents selected from hydroxy, oxo, $C_{1-4}$alkyl, $C_{1-4}$alkylCO, aryl, e.g. phenyl, or aralkyl, e.g benzyl, for instance morpholine or piperazine;

$R^{13}$ is COOH or a salt thereof, $COOR^{10}$, $CONR^{11}R^{12}$, CN or $CH_2OH$;

$R^{14}$ is an amino acid side chain such as $CH_2OH$ from serine;

$R^{15}$ and $R^{16}$ are independently hydrogen or $C_{1-4}$ alkyl e.g. methyl or ethyl;

$R^{17}$ and $R^{18}$ are independently hydrogen, $C_{1-15}$ alkyl, eg methyl or ethyl, $C_{1-10}$ alkoxy$C_{1-10}$ alkyl or aryl$C_{1-10}$ alkyl, e.g. benzyl;

$R^{19}$ together with the nitrogen atom to which it is attached forms a 5- to 7 membered ring optionally containing one or more further heteroatoms selected from oxygen, nitrogen and sulphur, and optionally substituted by one or two substituents selected from hydroxy, oxo, $C_{1-4}$ alkyl, aryl, e.g. phenyl, or aralkyl, e.g benzyl;

W is $SO_2$ or a bond;

X is O or S; and

Y is a group of the formula —$A^1$—$A^2$—$A^3$— in which $A^1$ and $A^3$ each represent a bond or a straight chain or branched alkylene group, said alkylene group(s) containing a total of 1 to 10 carbon atoms and $A^2$ represents a bond or O, S, SO, $SO_2$, CO, C=$CH_2$, CONH, NHCO, $CR^{15}R^{16}$, CH=CH or C≡C, providing that when $A^2$ is O, S, SO, $SO_2$ or CONH, $A^3$ contains at least two carbon atoms linking the $A^2$ group and the $CH_2$ group in formula (I).

Representative examples of $R^1$ include carboxy (COOH) and corresponding salts, esters ($COOR^{10}$) and amides ($CONR^{11}R^{12}$) thereof, for instance a sodium salt, an ethyl ester or an amide comprising an N-alkyl substituent, for instance, methyl, 2-methoxyethyl, octyl, dodecyl, N-benzyl, N-naphthylmethyl or a disubstitued amide comprising a combination thereof, or an amide in which the N forms part of a heterocyclic ring, for instance a piperidine ring.

Representative examples of the aromatic ring system represented by $R^2$ include phenyl and naphthyl. Representative examples of the heteroaromatic ring system which may be represented by $R^2$ include pyridyl, pyrimidinyl, pyrazolyl, furanyl, thienyl, thiazolyl, quinolyl, benzothiazolyl, pyridazolyl and pyrazinyl. Representative examples of $R^2$ include the phenyl group optionally substituted by 1, 2 or 3 substituents selected from halogen (e.g. chlorine or fluorine), $C_{1-4}$ alkyl (e.g. methyl or ethyl) or $C_{1-4}$ alkoxy (e.g. methoxy), for instance 4-fluorophenyl. Examples of the aryl and aralkyl substituents in the $R^2$ group include respectively phenyl and benzyl.

Representative examples of $R^3$ include $C_{1-20}$ alkyl, for instance methyl and undecyl, and $R^{17}R^{18}NHCOCH_2$ in which $R^{17}$ and $R^{18}$ is each independently $C_{1-15}$ alkyl, for instance $R^{17}$ is methyl and $R^{18}$ is methyl, octyl, or dodecyl.

Preferably, W is a bond.

Preferably, $R^3W$ is N-(1-Dodecyl)-N-methylaminocarbonylmethyl.

The group X is preferably S.

Preferred compounds of formula (I) include those in which Y is a bond, i.e. $A^1$, $A^2$ and $A^3$ each representing a bond. Other preferred examples of the groups $A^1$ and $A^3$ are straight chain alkylene groups. When $A^2$ is other than a bond, $A^1$ is preferably a bond. Preferred examples of $A^2$ above include CO, C=$CH_2$ and O, the CO group being especially preferred. Other preferred examples of Y are $(CH_2)_7$ or $CO(CH_2)_6$.

Pharmaceutically acceptable in vivo hydrolysable ester groups for $R^{10}$ include those which break down readily in the human body to leave the parent acid or its salt.

Representative examples of values of pharmaceutically acceptable in vivo hydrolysable ester groups for $R^{10}$ include:

—$CH(R^a)O.CO.R^b$;
—$CH(R^a)O.CO.OR^c$;
—$CH(R^a)CO.NR^eR^f$
—$R^dNR^eR^f$;
—$CH_2OR^g$;

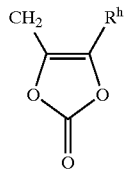

$CH(R^a)O.CO.C_6H_4Y^1COCH(R^i)NH_2$; and

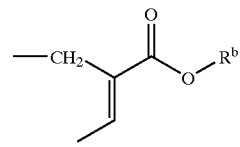

in which:

$R^a$ is hydrogen, $(C_{1-6})$alkyl, in particular methyl, $(C_{3-7})$cycloalkyl, or phenyl, each of which may be optionally substituted;

$R^b$ is $(C_{1-6})$alkyl, $(C_{1-6})$alkoxy$(C_{1-6})$alkyl, phenyl, benzyl, $(C_{3-7})$cycloalkyl, $(C_{1-6})$alkyl$(C_{3-7})$ cycloalkyl, 1-amino$(C_{1-6})$alkyl, or 1-$(C_{1-6}$alkyl) amino$(C_{1-6})$alkyl, each of which may be optionally substituted; or $R^a$ and $R^b$ together form a 1,2-phenylene group optionally substituted by one or two methoxy groups;

$R^c$ is $(C_{1-6})$alkyl, $(C_{3-7})$cycloalkyl, $(C_{1-6})$alkyl$(C_{3-7})$ cycloalkyl;

$R^d$ is $(C_{1-6})$alkylene optionally substituted with a methyl or ethyl group;

$R^e$ and $R^f$ which may be the same or different is each $(C_{1-6})$alkyl; or aryl$(C_{1-4})$alkyl, optionally substituted with e.g. hydroxy;

$R^g$ is $(C_{1-6})$alkyl;

$R^h$ is hydrogen, $(C_{1-6})$alkyl or phenyl;

$R^i$ is hydrogen or phenyl optionally substituted by up to three groups selected from halogen, $(C_{1-6})$-alkyl, or $(C_{1-6})$alkoxy; and $Y^1$ is oxygen or NH;

for instance:

(a) acyloxyalkyl groups such as acetoxymethyl, isobutyryloxymethyl, pivaloyloxymethyl, benzoyloxymethyl, α-acetoxyethyl, α-pivaloyloxyethyl, 1-(cyclohexylcarbonyloxy) ethyl, (1-aminoethyl)carbonyloxymethyl, 2-methoxyprop-2-ylcarbonyloxymethyl, phenylcarbonyloxymethyl and 4-methoxyphenylcarbonyloxymethyl;

(b) alkoxy/cycloalkoxycarbonyloxyalkyl groups, such as ethoxycarbonyloxymethyl, t-butyloxycarbonyloxymethyl, cyclohexyloxycarbonyloxymethyl, 1-methylcyclohexyloxycarbonyloxymethyl and α-ethoxycarbonyloxyethyl;

(c) dialkylaminoalkanol, especially di-loweralkylamino alkyl groups such as dimethylaminomethyl, dimethylaminoethyl, dimethylaminomethyl or diethylaminoethyl;

(d) acetamido groups such as N,N-dimethylaminocarbonylmethyl, N,N-(2-hydroxyethyl)aminocarbonylmethyl;

(e) lactone groups such as phthalidyl and dimethoxyphthalidyl;
(f) (5-methyl-2-oxo-1,3-dioxolen-4-yl)methyl; and
(g) (2-methoxycarbonyl-E-but-2-en-yl)methyl.

Representative examples of pharmaceutically acceptable in vivo hydrolysable ester groups for $R^{10}$ include:

(2-methoxycarbonyl-E-but-2-en-yl)methyl, isobutyryloxymethyl, 2-methoxyprop-2-ylcarbonyloxymethyl, phenylcarbonyloxymethyl, 4-methoxyphenyl-carbonyloxymethyl, t-butyloxycarbonyloxymethyl, cyclohexyloxycarbonyloxymethyl, 1-methylcyclohexyloxycarbonyloxymethyl, N,N-dimethylaminocarbonylmethyl, and (5-methyl-2-oxo-1,3-dioxolen-4-yl)methyl.

When used herein, the term "alkyl" and similar terms such as "alkoxy" include all straight chain and branched isomers.

It will be appreciated that in some instances, compounds of the present invention may include a carboxy group as a substituent. Such carboxy groups may be used to form salts, in particular pharmaceutically acceptable salts. Pharmaceutically acceptable salts include those described by Berge, Bighley, and Monkhouse, *J. Pharm. Sci.*, 1977, 66, 1–19. Preferred salts include alkali metal salts such as the sodium and potassium salts.

Compounds of formula (I) are inhibitors of Lp-PLA$_2$ and as such are expected to be of use in treating atherosclerosis and the other disease conditions noted elsewhere. Such compounds are found to act as inhibitors of Lp-PLA$_2$ in in vitro assays.

Particularly preferred compounds of formula (I) include:

1-(N-(1-Octyl)-N-methylaminocarbonylmethyl)-2-(4-fluorobenzyl)thio-5-(1-carboxymethyl-2-oxopyrimid-5-ylmethyl)pyrimidin-4-one;
1-(N-(1-Octyl)-N-methylaminocarbonylmethyl)-2-(4-fluorobenzyl)thio-5-(1-(methylaminocarbonylmethyl)-2-oxopyrimid-5-ylmethyl)pyrimidin-4-one;
1-(N-(1-Dodecyl)-N-methylaminocarbonylmethyl)-2-(4-fluorobenzyl)thio-5-(1-(methylaminocarbonylmethyl)-2-oxopyrimid-5-ylmethyl)pyrmidin-4-one;
1-(N-(1-Dodecyl)-N-methylaminocarbonylmethyl)-2-(4-fluorobenzyl)thio-5-(1-(1-morpholinocarbonylmethyl)-2-oxopyrimid-5-ylmethyl)pyrimidin-4-one; and
1-(N-(1-Dodecyl)-N-methylaminocarbonylmethyl)-2-(4-fluorobenzyl)thio-5-(1-carboxymethyl-2-oxopyrimid-5-ylmethyl)pyrimidin-4-one and the sodium salt thereof.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

Compounds of the present invention are inhibitors of the enzyme lipoprotein associated phospholipase A$_2$ (Lp-PLA$_2$) and as such are expected to be of use in therapy, in particular in the treatment of atherosclerosis. In a further aspect therefore the present invention provides a compound of formula (I) for use in therapy.

The compounds of formula (I) are inhibitors of lysophosphatidylcholine production by Lp-PLA$_2$ and may therefore also have a general application in any disorder that involves endothelial dysfunction, for example atherosclerosis, diabetes, hypertension, angina pectoris and after ischaemia and reperfusion. In addition, compounds of formula (I) may have a general application in any disorder that involves lipid peroxidation in conjunction with enzyme activity, for example in addition to conditions such as atherosclerosis and diabetes, other conditions such as rheumatoid arthritis, stroke, inflammatory conditions of the brain such as Alzheimer's Disease, myocardial infarction, reperfusion injury, sepsis, and acute and chronic inflammation. Further such conditions include various neuropsychiatric disorders such as schizophrenia (see Psychopharmacology Bulletin, 31, 159–165, 1995).

Further applications include any disorder that involves activated monocytes, macrophages or lymphocytes, as all of these cell types express Lp-PLA$_2$. Examples of such disorders include psoriasis.

Accordingly, in a further aspect, the present invention provides for a method of treating a disease state associated with activity of the enzyme Lp-PLA$_2$ which method involves treating a patient in need thereof with a therapeutically effective amount of an inhibitor of the enzyme. The disease state may be associated with the increased involvement of monocytes, macrophages or lymphocytes; with the formation of lysophosphatidylcholine and oxidised free fatty acids; with lipid peroxidation in conjunction with Lp PLA2 activity; or with endothelial dysfunction.

Compounds of the present invention may also be of use in treating the above mentioned disease states in combination with anti-hyperlipidaemic or anti-atherosclerotic or anti-diabetic or anti-anginal or anti-inflammatory or anti-hypertension agents. Examples of the above include cholesterol synthesis inhibitors such as statins, anti-oxidants such as probucol, insulin sensitisers, calcium channel antagonists, and anti-inflammatory drugs such as NSAIDs.

In therapeutic use, the compounds of the present invention are usually administered in a standard pharmaceutical composition. The present invention therefore provides, in a further aspect, a pharmaceutical composition comprising a compound of formula (I) and a pharmaceutically acceptable carrier.

Suitable pharmaceutical compositions include those which are adapted for oral or parenteral administration or as a suppository. Compounds of formula (I) which are active when given orally can be formulated as liquids, for example syrups, suspensions or emulsions, tablets, capsules and lozenges. A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Typical parenteral compositions consist of a solution or suspension of the compound of formula (I) in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration. A typical suppository formulation comprises a compound of formula (I) which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule. Each dosage unit for oral administration contains preferably from 1 to 500 mg (and for parenteral administration contains preferably from 0.1 to 25 mg) of a compound of the formula (I). The daily dosage regimen for an adult patient may be, for example, an oral dose of between 1 mg and 1000 mg, preferably between 1 mg and 500 mg, or an intravenous, subcutaneous, or intramuscular dose of between 0.1 mg and 100 mg, preferably between 0.1 mg and 25 mg, of the compound of the formula (I), the compound being administered 1 to 4 times per day. Suitably the compounds will be administered for a period of continuous therapy, for example for a week or more.

Compounds of formula (I) may be conveniently prepared by a process which comprises reacting a compound of formula (II):

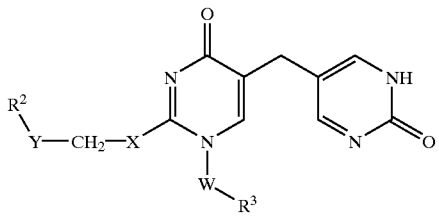

in which
$R^2$, $R^3$, W, X and Y are as hereinbefore defined;
with an alkylating agent of formula $R^1$—$CH_2$—$L^1$ in which $R^1$ is as hereinbefore defined and $L^1$ is a leaving group such as chloride, bromide, iodide or mesylate, in the presence of a base such as potassium carbonate; and thereafter, and if necessary,
interconverting groups in $R^1$, for example $COOR^{10}$ to COOH by standard conditions (alkaline hydrolysis, hydrogenation of benzyl ester, etc), or COOH to $CONR^{11}R^{12}$ by amide coupling.

A compound of formula (II) can conveniently by prepared by O-dealkylation of the corresponding compound of formula (III):

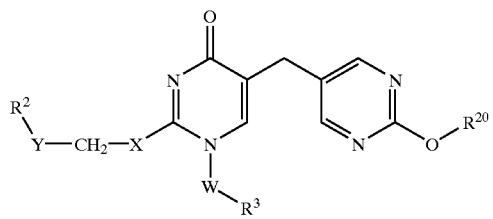

in which
$R^{20}$ is $C_{1-4}$ alkyl, arylmethyl or diarylmethyl and $R^2$, $R^3$, W, X and Y are as hereinbefore defined. Typical conditions include treatment with boron tribromide or B-bromocatecholborane in dichloromethane at temperatures between −20° and ambient;
hydrogenolysis of benzyloxy groups; acid cleavage of O-tBu.

A compound of formula (III) may be readily prepared in a series of steps from a compound of formula (IV):

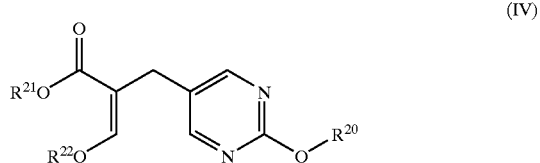

in which
$R^{21}$ is hydrogen or $C_{1-4}$alkyl, for instance methyl or ethyl, $R^{22}$ is hydrogen or methyl and $R^{20}$ is as hereinbefore defined;
using procedures well known in the art for thiouracil formation, N-alkylation and thioetherification.

Thus, for instance, for a compound of formula (III) in which W is a bond, a compound of formula (IV) in which $R^{21}$ is hydrogen and $R^{22}$ is methyl may be treated with oxalyl chloride in a dry solvent such as dichloroethane, to form an intermediate acyl chloride, followed by treatment with potassium thiocyanate in the presence of a solvent such as acetonitrile, and then treatment with a compound of the formula (V):

$R^3WNH_2$ (V)

in which W is a bond and $R^3$ is as hereinbefore defined; followed by the addition of a base such as sodium ethoxide, to give a thiouracil compound of the formula (VI):

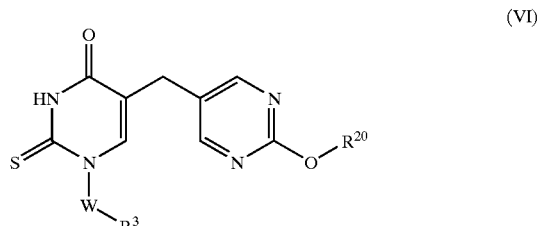

in which $R^3$, $R^{20}$ and W are as hereinbefore defined. The compound of formula (VI) may then be treated with a compound of the formula (VII):

$$R^2YCH_2L^1 \quad (VII)$$

in which $L^1$ and $R^2$ are as hereinbefore defined; to give a compound of formula (III) in which X is S.

In an alternative approach, a compound of formula (IV) in which $R^{21}$ is $C_{1-4}$alkyl, for instance methyl, and $R^{22}$ is methyl, may be treated with thiourea, to form a thiouracil of the formula (VIII):

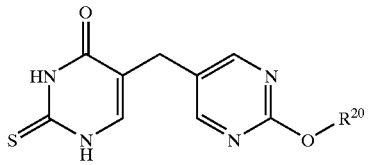

(VIII)

in which $R^{20}$ is a hereinbefore defined. This thiouracil may then be treated with a compound of the formula (VII) as hereinbefore described, to give a compound of formula (IX):

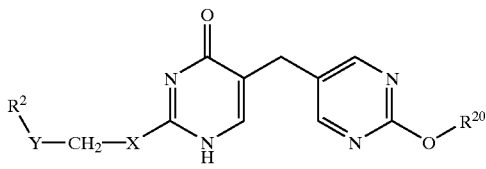

(IX)

in which $R^2$, $R^{20}$ and Y are as hereinbefore defined and X is S. Subsequent reaction of a compound of formula (IX) with a compound of the formula (X):

$$R^3WL^1 \quad (X)$$

in which $L^1$, $R^3$ and W are as hereinbefore defined; leads to a compound of formula (III) in which X is S.

Compounds of formula (IV) may be readily obtained from a convenient, readily available pyrimdine starting material such as a 2-alkoxy 5-bromopyrimidine, using processes well known in the art. This pyrimidine may be coupled with an acrylate ester such as ethyl or methyl acrylate, using a Heck reaction, and the intermediate then subjected to catalytic hydrogenation to give a propionic acid ester derivative. This in turn may be treated with methyl formate in the presence of a strong base such as potassium t-butoxide or sodium hydride, to give a compound of formula (IV) in which $R^{22}$ is hydrogen. Alkylation, for instance methylation, using dimethyl sulphate, then gives a compound of formula (IV) in which $R^{22}$ is alkyl. A compound of formula (IV) in which $R^{21}$ is hydrogen (ie the carboxylic acid) may be obtained from the corresponding ester by hydrolysis under basic conditions, for instance aqueous sodium hydroxide.

Compounds of formula (I) in which X is O may be conveniently be prepared from corresponding compounds of formula (I) in which X is S by treatment thereof with a compound of the formula (XI):

$$R^2YCH_2OH \quad (XI)$$

in which $R^2$ is as hereinbefore defined.

The present invention will now be illustrated by the following examples:

INTERMEDIATE 1

N-(1-Dodecyl)-N-methylbromoacetamide

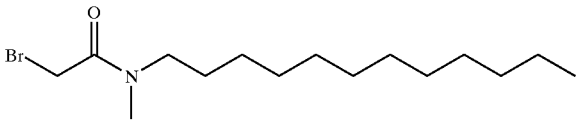

To a solution of N-methyl-N-dodecylamine (2.5 ml) and triethylamine (1.4 ml) in dichloromethane (10 ml) was added with stirring and ice cooling a solution of bromoacetyl bromide (0.87 ml) in dichloromethane (10 ml). The cooling bath was removed after 30 min and the reaction stood for 16 h at ambient temperature. The mixture was washed with water and saturated sodium hydrogen carbonate, dried ($K_2CO_3$) and the solution purified by flash chromatography (silica, methanol-dichloromethane). Appropriate fractions were combined and evaporated to a pale yellow oil, yield 1.53 g (48%). $^1$H-NMR (CDCl$_3$) δ0.8 (3H,t), 1.2 (18H,m), 1.5 (2H,m,), 2.88 and 2.99 (3H,2xs), 3.27 (2H,m), 3.77 and 3.79 (2H,s)); MS (APCI+) found (M+1)=320, 322, $C_{15}H_{30}BrNO$ requires 319,321.

INTERMEDIATE 2

N-(1-Octyl)-N-methylbromoacetamide

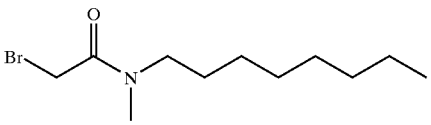

Prepared analogously to intermediate 1, from N-methyl-N-octylamine. $^1$H-NMR (CDCl$_3$) δ0.85–1.0 (3H,m), 1.1–1.4 (10H,m), 1.4–1.75 (2H,m,), 2.95 and 3.07 (3H, 2xs), 3.25–3.45 (2H,m), 3.85 and 3.86 (2H,s)); MS (APCI+) found (M+1)=264, 266, $C_{15}H_{30}BrNO$ requires 319,321.

INTERMEDIATE 3

Ethyl 3-(2-methoxypyrimidin-5-yl)acrylate

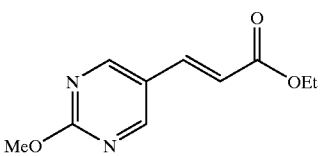

A mixture of 2-methoxy-5-bromopyrimidine (75.43 g, 0.399 mol), ethyl acrylate (47.5 ml, 0.439 mol), palladium (II) acetate (1.07 g, 0.0048 mol), tri-o-tolylphosphine (2.92 g, 0.0096 mol) and triethylamine (84 ml) were heated at 135° C. with stirring under argon for 12 h. After allowing to cool the solid mass was dissolved in water and ethyl acetate, filtered, and the aqueous phase separated and further extracted with ethyl acetate. The combined extracts were washed with saturated aqueous ammonium chloride, dried (MgSO$_4$) and evaporated. The solid thus obtained was triturated with ether/light petrol (1:3, 350 ml), filtered, washed and dried, yield 52.41 g (63%). $^1$H-NMR (CDCl$_3$) δ1.33 (3H, t), 4.06 (3H, s), 4.28 (2H, q), 6.45 (1H, d), 7.58 (1H, d), 8.67 (2H, s); MS (APCI+) found (M+H)=209; $C_{10}H_{12}N_2O_3$ requires 208.

INTERMEDIATE 4

Ethyl 3-(2-methoxypyrimidin-5-yl)propionate

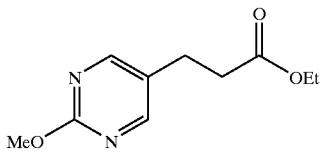

A suspension of ethyl 3-(2-methoxypyrimidin-5-yl) acrylate (52.4 g, 0.252 mol) in ethanol (400 ml) and triethylamine (50 ml) was treated with 10% palladium on carbon (3 g) and hydrogenated at 50 psi for 1.75 h. The catalyst was filtered off through hyflo and the filtrate evaporated. The residue was dissolved in dichloromethane, washed twice with saturated aqueous ammonium chloride, dried (MgSO$_4$) and evaporated to an oil, yield 41.2 g (78%). $^1$H-NMR (CDCl$_3$) δ1.23 (3H, t), 2.61 (2H, t), 2.87 (2H, t), 3.99 (3H, s), 4.13 (2H, q), 8.39 (2H, s); MS (APCI+) found (M+H)=211; C$_{10}$H$_{14}$N$_2$O$_3$ requires 210.

INTERMEDIATE 5

2-(Methoxymethylene)-3-(2-methoxypyrimidin-5-yl) propionic acid, mixed methylethyl esters

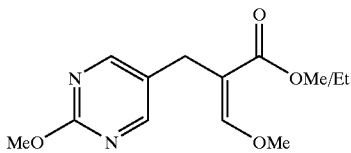

To a stirring suspension of sodium hydride (0.83 g of a 60% dispersion in oil) in anhydrous 1,2-dimethoxyethane (6 ml) was added dropwise a solution of methyl formate (1.54 ml) and ethyl 3-(2-methoxypyrimid-5-yl)propionate (3.5 g) in anhydrous 1,2-dimethoxyethane (6 ml) at such a rate as to maintain the reaction temperature at 25–30° C. After 1 h, ether was added and the precipitated oil allowed to settle. The solution was decanted off and replaced with fresh ether, and the oil slowly solidified. The solid 2-(hydroxymethylene) derivative was filtered, washed and dried, yield 3.8 g. A 1.33 g portion was suspended in dimethyl formamide (10 ml) together with anhydrous potassium carbonate (1.15 g), and a solution of dimethyl sulphate (0.48 ml) in dimethylformamide (10 ml) was added dropwise with stirring over 30 min. After 16 h the solvent was evaporated and the residue treated with water and extracted with ethyl acetate. The extracts were washed with water, dried (MgSO$_4$) and evaporated to give the product as an oil, yield 0.91 g. $^1$H-NMR (CDCl$_3$) δ1.23 (3H, t), 3.46 (2H, s), 3.69 (3H, s, methyl ester), 3.88 (3H, s), 3.97 (3H, s), 4.16 (2H, q), 7.39 (1H, s), 8.40 (2H, s). 3:2 ratio of methyl:ethyl esters. MS (APCI+) found (M+1)=253, 239 (ethyl and methyl esters); C$_{12}$H$_{16}$N$_2$O$_4$ requires 252, C$_{11}$H$_{14}$N$_2$O$_4$ requires 238.

INTERMEDIATE 6

2-(Methoxymethylene)-3-(2-methoxypyrimidin-5-yl) propionic acid

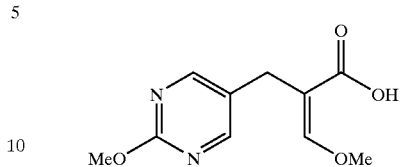

A suspension of the mixed esters of intermediate 5 (0.9 g) in 2M aqueous sodium hydroxide (3.6 ml) was stirred at ambient temperature for 16 h to give a clear solution. This was diluted with water, extracted with dichloromethane and evaporated to about half volume, then acidified to pH 3–4 (2M hydrochloric acid) when the product crystallised out. The white solid was filtered, washed with ice-cold water and dried, yield 0.46 g. $^1$H-NMR (CDCl$_3$) δ3.43 (2H, s), 3.91 (3H, s), 3.99 (3H, s,), 7.49 (1H, s), 8.42 (2H, s); MS (APCI+) found (M+1)=225, C$_{10}$H$_{12}$N$_2$O$_4$ requires 224.

INTERMEDIATE 7

5-(2-Methoxypyrimidin-5-ylmethyl)-2-thiouracil

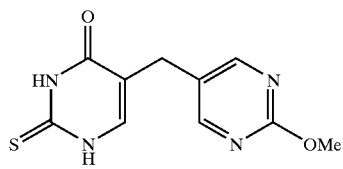

To an ice cooled solution of potassium t-butoxide (7.83 g, 0.07 mol) in anhydrous THF (60 ml) was added dropwise with stirring under argon over 1 hour to a solution of ethyl 3-(2-methoxypyrimidin-5-yl)propionate (5.87 g, 0.028 mol) and methyl formate (3.6 ml, 0.059 mol) in anhydrous ether (70 ml). After stirring for 16 h, the solvents were evaporated, thiourea (4.25 g, 0.056 mol) and propan-2-ol (80 ml) added and the mixture refluxed for 5 h. The solvent was evaporated and the residue dissolved in water, extracted twice with ether and acidified to pH 4.5 with acetic acid. The solid which precipitated was filtered, washed well with water and dried, yield 5.57 g (80%). $^1$H-NMR (d$_6$-DMSO) δ3.47 (2H, s), 3.85 (3H, s), 7.43 (1H, s), 8.48 (2H, s), 12.25 (1H, br s), 12.46 (1H, br s); MS (APCI+) found (M+H)=251; C$_{10}$H$_{10}$N$_4$O$_2$S requires 250.

INTERMEDIATE 8

1-(1-Undecyl)-5-(2-ethoxypyrimidin-5-ylmethyl)-2-thiouracil

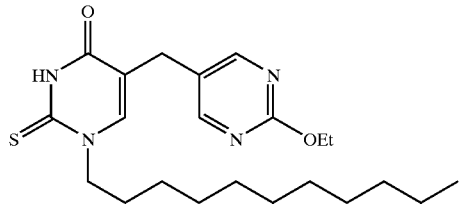

To a slurry of 2-(methoxymethylene)-3-(2-methoxypyrimidin-5-yl)propionic acid (3.1 g) in dry dichloroethane (50 ml) was added oxalyl chloride (2.5 ml). The mixture was stirred at room temperature for 4 h and the solvent was removed in vacuo. Further dichloroethane (50 ml) was added and removed in vacuo. The residue was mixed with acetonitrile (50 ml) and dry potassium thiocyanate (2.0 g) added. The mixture was stirred under argon for 21 h and the solvent removed in vacuo. The residue was mixed with dimethylformamide and 1-undecylamine (3.0 ml) added with stirring, followed by triethylamine (5 ml). The mixture was stirred at room temperature under argon for 20 h and a solution of sodium ethoxide in ethanol (3M, 19 ml) was added. The reaction was heated at 90° C. for 2 h, cooled and the solvent was removed in vacuo. The residue was dissolved in water and glacial acetic acid was added to pH4.5. The solid so formed was filtered, evaporated with ethanol (100 ml) in vacuo and dried in vacuo to give the desired product (5 g). $^1$H-NMR (d$_6$ DMSO) δ0.75–0.95 (3H,m), 1.1–1.8 (21H,m), 3.49 (2H,s), 4.11 (2H,t), 4.31 (2H,q), 7.87 (1H,s) 8.47 (2H,s); MS (APCI+) found (M+1)= 419; C$_{22}$H$_{34}$N$_4$O$_2$S requires 418.

INTERMEDIATE 9

1-(1-Undecyl)-5-(2-methoxypyrimid-5-ylmethyl)-2-thiouracil

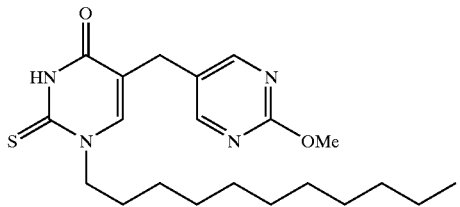

Prepared analogously to intermediate 8, except using sodium methoxide in place of ethoxide. $^1$H-NMR (CDCl$_3$) δ0.8–0.95 (3H,t), 1.1–1.85 (18H,m), 3.59 (2H, s), 4.01 (3H,s), 4.11 (2H,t), 7.04 (1H,s), 8.43 (2H, s); MS (APCI+) found (M+1)=405; C$_{21}$H$_{32}$N$_4$O$_2$S requires 404.

INTERMEDIATE 10

1-(1-Undecyl)-2-(4-fluorobenzylthio)-5-(2-ethoxypyrimid-5-ylmethyl)pyrimidin-4-one

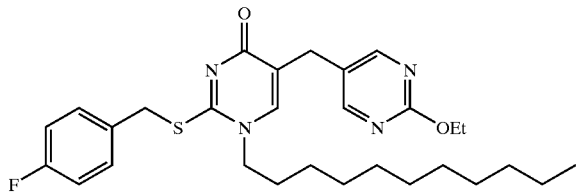

To a mixture of 1-undecyl-5-(2-ethoxypyrimidin-5-ylmethyl)-2-thiouracil (5.0 g) and diisopropylethylamine (2.1 ml) in dry methylene chloride (200 ml) was added 4-fluorobenzyl bromide (1.5 ml) and the mixture stirred under argon at room temperature for 20 h. The solution was washed with 5% aqueous sodium bicarbonate and the organic layer was added directly to a silica gel column (200 g). Elution with ethyl acetate to 5% methanol in ethyl acetate gave the desired product (2.7 g). $^1$H-NMR (CDCl$_3$) δ0.8–0.95 (3H,m), 1.15–1.4 (16H,m), 1.43 (3H,t), 1.55–1.8 (2H,m), 3.68 (2H,s), 3.71 (2H,t), 4.41 (2H,q), 4.47 (2H,s), 6.86 (1H,s), 6.9–7.1 (2H,m), 7.3–7.45 (2H,m), 8.45 (2H,d); MS (APCI+) found (M+1)=527; C$_{29}$H$_{39}$FN$_4$O$_2$S requires 526.

INTERMEDIATE 11

2-(4-Fluorobenzylthio)-5-(2-methoxypyrimid-5-ylmethyl)pyrimidin-4-one

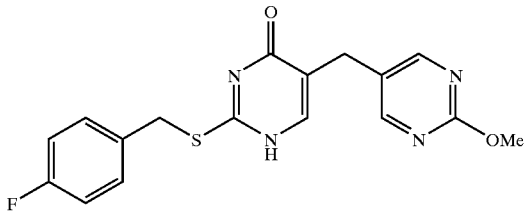

Prepared analogously to intermediate 10, from 5-(2-methoxypyrimidin-5-ylmethyl)-2-thiouracil. $^1$H-NMR (d$_6$ DMSO) δ3.55 (2H,s), 3.85 (3H,s), 4.36 (2H,s), 7.0–7.2 (2H,m), 7.35–7.5 (2H,m), 7.86 (1H,bs), 8.48 (2H,s) 12.81 (1H,b); MS (APCI+) found (M+1)=359; C$_{17}$H$_{15}$FN$_4$O$_2$S requires 358.

INTERMEDIATE 12

1-Methyl-2-(4-fluorobenzylthio)-5-(2-methoxypyrimid-5-ylmethyl)pyrimidin-4-one

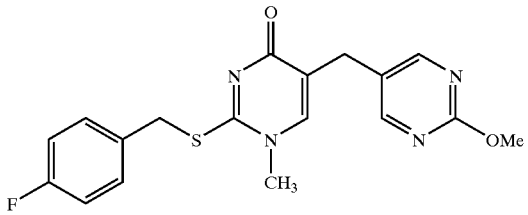

To a solution of intermediate 11 (10.2 g) and diisopropylethylamine (6.0 ml) in dry methylene chloride (120 ml) was added iodomethane (1.7 ml) under argon with stirring. The mixture was left at room temperature for 48 h, washed with saturated ammonium chloride and saturated sodium bicarbonate and added directly to a silica (200 g) column. Elution with 2% to 10% methanol in ethyl acetate gave the desired product (2.5 g). $^1$H-NMR (CDCl3) δ3.47 (3H,s), 3.64 (2H,t), 3.99 (3H,s), 4.47 (2H,s), 6.88 (1H,s), 6.9–7.1 (2H,m), 7.3–7.5 (2H,m), 8.44 (2H,s); MS (APCI+) found (M+1)= 373; C$_{18}$H$_{17}$FN$_4$O$_2$S requires 372.

INTERMEDIATE 13

1-(N-Methyl-N-(1-octyl)aminocarbonylmethyl)-2-(4-fluorobenzylthio)-5-(2-methoxypyrimid-5-ylmethyl)pyrimidin-4-one

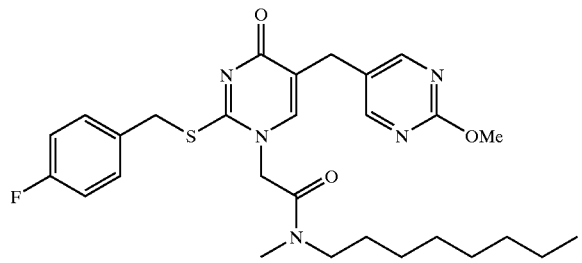

Prepared analogously to intermediate 12, using N-(1-octyl)-N-methylbromoacetamide in place of iodomethane. $^1$H-NMR (CDCl$_3$) δ0.8–0.95 (3H,m), 1.1–1.7 (12H,m), 2.95 and 2.99 (3H,2xs), 3.21 and 3.36 (2H, 2xt), 3.66 (2H,s), 3.99 (3H,s), 4.48 (2H,s), 4.51 and 4.55 (2H,d), 6.80 (1H,s), 6.9–7.1 (2H,m), 7.3–7.45 (2H,m), 8.45 (2H,s); MS (APCI+) found (M+1)=542; C$_{28}$H$_{36}$FN$_5$O$_3$S requires 541.

INTERMEDIATE 14

1-(N-Methyl-N-(1-dodecyl)aminocarbonylmethyl)-2-(4-fluorobenzylthio)-5-(2-methoxypyrimid-5-ylmethyl)pyrimidin-4-one

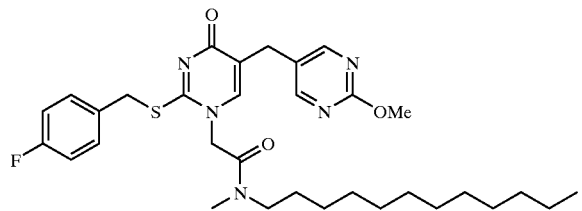

A mixture of N-dodecyl-N-methylbromoacetamide (1.53 g), 2-(4-fluorobenzylthio)-5-(2-methoxypyrimidyl-5-ylmethyl)pyrimid4-one (1.71 g) and N,N-diisopropylethylamine (0.92 ml) in dichloromethane (7 ml) was stirred at ambient temperature for 16 h. The solution was washed with saturated ammonium chloride then purified by flash chromatography (fine silica, methanol-ethyl acetate) to give the product as a solid, yield 0.82 g (29%). $^1$H-NMR (CDCl$_3$) δ0.85 (3H,t), 1.2 (18H,m), 1.5 (2H,m,), 2.92 and 2.95 (3H,2xs), 3.17 and 3.33 (2H,2xm), 3.63 (2H,s), 3.96 (3H,s), 4.45 (2H,s), 4.49 and 4.52 (2H,2xs), 6.79 (1H,s), 6.95 (2H,m), 7.30 (2H,m), 8.42 (2H,s); MS (APCI+) found (M+1)=598, C$_{32}$H$_{44}$FN$_5$O$_3$S requires 597.

INTERMEDIATE 15

1-(1-Undecyl)-2-(4-fluorobenzyl)thio-5-(2-methoxypyrimid-5-ylmethyl)pyrimidin-4-one

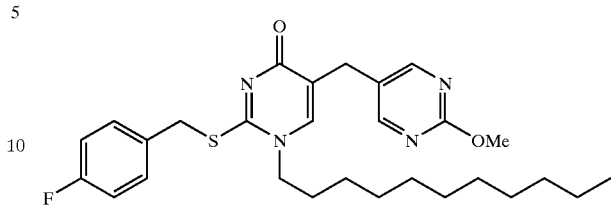

Prepared analogously to intermediate 10, from 1-undecyl-5-(2-methoxypyrimidin-5-ylmethyl)-2-thiouracil $^1$H-NMR (CDCl$_3$) δ0.88 (3H, t), 1.25 (16H, m), 1.68 (2H, m), 3.64 (2H, s), 3.71 (2H, t), 4.00 (3H, s), 4.47 (2H, s), 6.87 (1H, s), 7.00 (2H, m), 7.36(2H, m), 8.46(2H, s); MS (APCI+) found (M+H)=513; C$_{28}$H$_{37}$N$_4$O$_2$S requires 512.

INTERMEDIATE 16

1-(1-Undecyl)-2-(4-fluorobenzyl)thio-5-(2-oxopyrimid-5-ylmethyl)pyrimidin-4-one

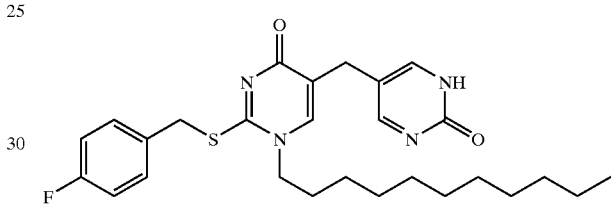

To a solution of intermediate 15 (0.2 g) in dry methylene chloride (4 ml) at 4° C. was added boron tribromide (1M in methylene chloride, 2 ml). The mixture was stirred under argon for 24 h and poured into a mixture of ice (50 ml) and 0.880 ammonia (15 ml) with stirring. Extraction with 5% methanol in methylene chloride was followed by filtration through kieselguhr and drying the organic layer over sodium sulphate. Removal of the solvent in vacuo gave the desired material as a grey solid (0.15 g). The same material could be prepared from intermediate 10 by an identical method. $^1$H-NMR (CDCl$_3$) δ0.8–0.95 (3H,m), 1.1–1.4 (16H,m), 1.6–1.85 (2H,m), 3.49 (2H,s), 3.79 (2H,t), 4.45 (2H,s), 6.9–7.1 (2H,m), 7.2–7.45 (3H,m), 8.32 (2H,s); MS (APCI+) found (M+1)=499; C$_{27}$H$_{35}$FN$_4$O$_2$S requires 498.

INTERMEDIATE 17

1-(N-Methyl-N-(1-octyl)aminocarbonylmethyl)-2-(4-fluorobenzyl)thio-5-(2-oxopyrimid-5-ylmethyl)pyrimidin-4-one

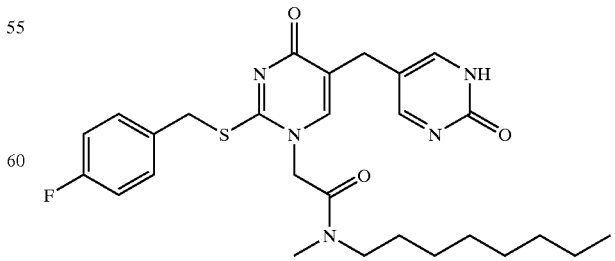

Prepared analogously to intermediate 16, from 1-(N-methyl-N-(1-octyl)-aminocarbonylmethyl)-2-(4- fluorobenzylthio)-5-(2-methoxypyrimid-5-ylmethyl)-pyrimidin-4-one, except that the reaction was performed at 5° C. (ice-bath) for 4–6 h. $^1$H-NMR (d$_6$ DMSO) δ0.8–0.95 (3H,m), 1.05–1.65 (12,m), 2.81 and 2.94(3H,2xs), 3.15–3.4 (4H,m), 4.39 (2H,s), 4.83 and 4.85 (2H,2xd), 7.05–7.2 (2H,m), 7.35–7.55 (3H,m), 7.95–8.35 (2H,b); MS (APCI+) found (M+1)=526; C$_{27}$H$_{35}$FN$_4$O$_2$S requires 525.

INTERMEDIATE 18

1-Methyl-2-(4-fluorobenzyl)thio-5-(2-oxopyrimid-5-ylmethyl)pyrimidin-4-one

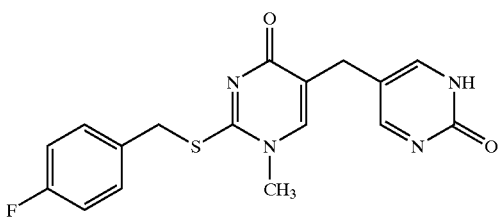

To a solution of intermediate 12 (5 g) in dry methylene chloride was added a solution of boron tribromide 1M in dichloromethane (50 ml) at 5° C. under argon with stirring. After 0.5 h, the mixture was allowed to warm to room temperature and was allowed to stir at room temperature for 72 h. The mixture was decanted into a mixture of ice (50 ml) and 0.880 ammonia (50 ml). The solid remaining in the flask was treated with some of the aqueous mixture and 10% methanol in methylene chloride. The entire mixture was filtered through kieselguhr and the organic layer was separated. The aqueous layer was reduced to one quarter volume in vacuo and the solid formed filtered off, washed with water and dried in vacuo to give the desired product (2.2 g). $^1$H-NMR (d$_6$ DMSO) δ3.30 (2H,s), 3.47 (3H,s), 4.41 (2H,s), 7.05–7.25 (2H,m), 7.4–7.55 (2H,m), 7.65 (1H,s), 7.85–8.3 (2H,b); MS (APCI+) found (M+1)=359; C$_{17}$H$_{15}$FN$_4$O$_2$S requires 358.

EXAMPLE 1

1-(1-Undecyl)-2-(4-fluorobenzyl)thio-5-(1-(ethoxycarbonylmethyl)-2-oxopyrimid-5-ylmethyl)pyrimidin-4-one

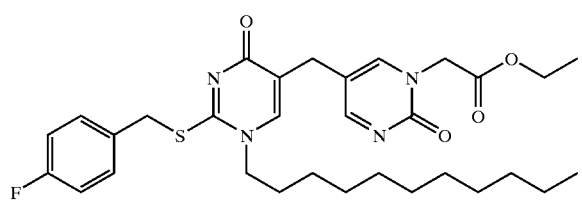

To a solution of intermediate 16 (0.64 g) in dry dimethylformamide (15 ml) was added ethyl bromoacetate (0.15 ml) and potassium carbonate (0.38 g). The mixture was heated at 70° C. for 3 h under argon with stirring. The dimethylformamide was removed in vacuo and the residue was partitioned between aqueous ammonium chloride (30 ml) and methylene chloride. The aqueous layer was washed with further methylene chloride and the combined organic layers were added directly to a SepPak cartridge (SiO$_2$, 10 g) and eluted with 0–15% methanol in ethyl acetate. This gave the desired product as a gum (0.63 g). $^1$H-NMR (CDCl3) δ0.8–0.95 (3H,m), 1.15–1.4 (19H,m), 1.65–1.85 (2H,m), 3.47 (2H,s), 3.7 (2H,t), 4.25 (2H,q), 4.46 (2H,s), 4.61 (2H,s), 6.9–7.1 (2H,m), 7.12 (1H,s), 7.3–7.45 (2H,m), 7.87 (1H,bd), 8.5 (1H,bd); MS (APCI+) found (M+1)=585; C$_{31}$H$_{41}$FN$_4$O$_4$S requires 584.

EXAMPLE 2

1-(1-Undecyl)-2-(4-fluorobenzyl)thio-5-(1-(carboxymethyl)-2-oxopyrimid-5-ylmethyl)pyrimidin-4-one

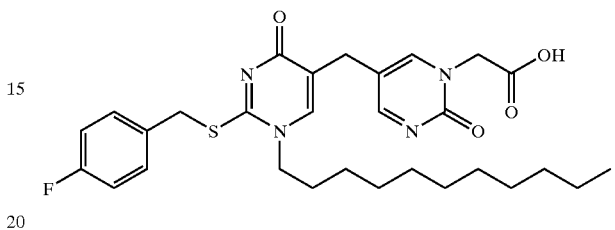

A solution of sodium hydroxide (0.023 g) in water (1.25 ml) was added to a solution of 1-undecyl-2-(4-fluorobenzyl)thio-5-(1-(carbethoxymethyl)-2-oxopyrimid-5-ylmethyl)pyrimidin-4-one (0.33 g) in dioxan (5 ml) under argon. After 16 h, the solvent was removed, almost to dryness, in vacuo and the residue dissolved in water (30 ml). Acidification to pH 1 with 2M hydrochloric acid gave a solid that was filtered, washed with water and dried in vacuo to give the desired product (0.14 g) as a white solid. $^1$H-NMR (d$_6$ DMSO) δ0.8–0.95 (3H,m), 1.1–1.4 (16H,m), 1.55–1.8 (2H, m), 3.38 (2H,s), 3.81 (2H,t), 4.42 (2H,s), 4.62 (2H,s), 7.05–7.2 (2H,m), 7.4–7.55 (2H,m), 7.80 (1H,s), 8.22 (1H, bd), 8.65 (1H,bd).

EXAMPLE 3

1-(1-Undecyl)-2-(4-fluorobenzyl)thio-5-(1-(dimethylaminocarbonylmethyl)-2-oxopyrimid-5-ylmethyl)pyrimidin4-one

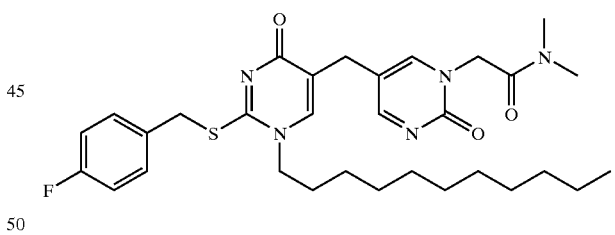

A mixture of 1-undecyl-2-(4-fluorobenzyl)thio-5-(1-(carboxymethyl)-2-oxopyrimid-5-ylmethyl)pyrimidin-4-one, dimethylamine hydrochloride (0.02 g), diisopropylethylamine (0.045 ml), hydroxybenzotriazole (0.005 g) and 1-(3-dimethylaminopropyl)-3-ethylcarbodiimide hydrochloride (0.045 g) in dry methylene chloride were stirred together for 24 h and diluted with 3% methanol in methylene chloride and 5% aqueous potassium carbonate. The organic layer was added directly to a SepPak cartridge (SiO$_2$, 10 g) and eluted with 0–20% methanol in ethyl acetate to give the desired product (0.085 g). $^1$H-NMR (CDCl$_3$) δ0.8–0.95 (3H,m), 1.15–1.4 (16H,m), 1.6–1.85 (2H,m), 2.98 (3H,s), 3.13 (3H,s), 3.49 (2H,s), 3.77 (2H,t), 4.46 (2H,s), 4.74 (2H,s), 6.9–7.1 (2H,m), 7.14 (1H,s), 7.3–7.45 (2H,m), 7.78 (1H,bd), 8.49 (1H,bd); MS (APCI+) found (M+1)=584; C$_{31}$H$_{42}$FN$_5$O$_3$S requires 583.

EXAMPLE 4

1-Methyl-2-(4-fluorobenzyl)thio-5-(1-(ethoxycarbonylmethyl)-2-oxopyrimid-5-ylmethyl)pyrimidin-4-one

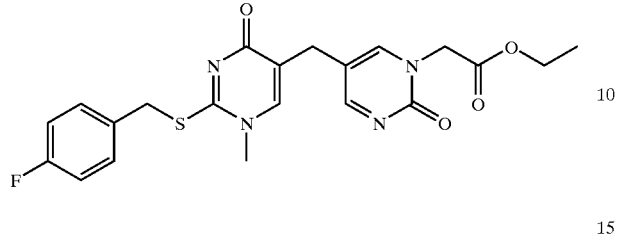

Prepared analogously to example 1. $^1$H-NMR (CDCl$_3$) δ1.30 (3H,t), 3.48 (2H,s), 3.54 (3H,s), 4.22 (2H,q), 4.45 (2H,s), 4.61 (2H,s), 6.9–7.1 (2H,m), 7.3–7.5 (3H,m), 7.91 (1H,d), 8.6 (1H,d); MS (APCI+) found (M+1)=445; C$_{21}$H$_{21}$FN$_4$O$_4$S requires 444.

EXAMPLE 5

1-Methyl-2-(4-fluorobenzyl)thio-5-(1-(carboxymethyl)-2-oxopyrimid-5-ylmethyl)pyrimidin4-one

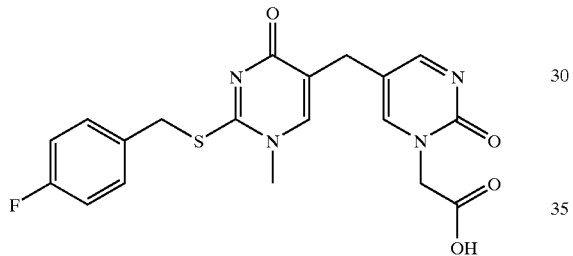

Prepared analogously to example 2. $^1$H-NMR (d$_6$ DMSO) δ3.34 (2H,s), 3.48 (3H,t), 4.42 (2H,s), 4.55 (2H,s), 7.05–7.2 (2H,m), 7.4–7.6 (2H,m), 7.70 (1H,s), 8.01 (1H,bd), 8.58 (1H,bd).

EXAMPLE 6

1-Methyl-2-(4-fluorobenzyl)thio-5-(1-(1-octylaminocarbonylmethyl)-2-oxopyrimid-5-ylmethyl)pyrimidin-4-one

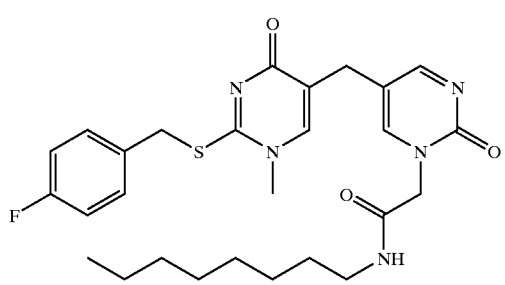

Prepared analogously to example 3. $^1$H-NMR (d$_6$ DMSO) δ0.8–0.95 (3H,t), 1.2–1.55 (12H, m), 3.05–3.2 (2H,m), 3.39 (2H,s), 3.52 (3H,s), 4.44 (2H.s), 4.47 (2H,s), 6.95–7.15 (2H,m), 7.4–7.55 (2H,m), 7.67 (1H,s) 7.95 (1H,d), 8.56 (1H,d); MS (APCI+) found (M+1)=528; C$_{27}$H$_{34}$FN$_5$O$_3$S requires 527.

EXAMPLE 7

1-Methyl-2-(4-fluorobenzyl)thio-5-(1-(N-benzyl-N-methylamino-carbonylmethyl)-2-oxopyrimid-5-ylmethyl)pyrimidin-4-one

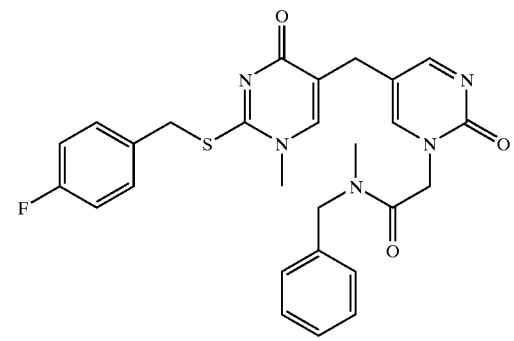

Prepared analogously to example 3. $^1$H-NMR (CDCl$_3$) δ3.00 and 3.04 (3H,2xs), 3.5 (3H,s+2H,s), 4.47 (2H,s), 4.55–4.9 (2H,s), 6.9–7.1 (2H,m), 7.15–7.55 (8H,m), 7.75–7.9 (1H,m), 8.45–8.6 (1H,m).

EXAMPLE 8

1-Methyl-2-(4-fluorobenzyl)thio-5-(1-(N-(1-dodecyl)-N-methylamino-carbonylmethyl)-2-oxopyrimid-5-ylmethyl)pyrimidin-4-one

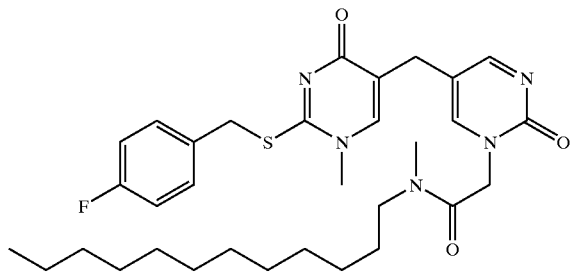

Prepared analogously to example 3. $^1$H-NMR (CDCl$_3$) δ0.8–0.95 (3H,m), 1.1–1.75 (20H,m), 2.97 and 3.09 (3H, 2xs), 3.35 (2H,t), 3.49 (2H,s), 3.52 (3H,s), 4.47 (2H,s), 4.72 (2H,s), 6.9–7.1 (2H,m), 7.23 (1H,s), 7.3–7.5 (2H,m), 7.77 (1H,bd), 8.48 (1H,bd); MS (APCI+) found (M+1) 598; C$_{32}$H$_{44}$FN$_5$O$_3$S requires 597.

EXAMPLE 9

1-Methyl-2-(4-fluorobenzyl)thio-5-(1-(N-(2-methoxyethyl)-N-methyl-aminocarbonylmethyl)-2-oxopyrimid-5-ylmethyl)pyrimidin-4-one

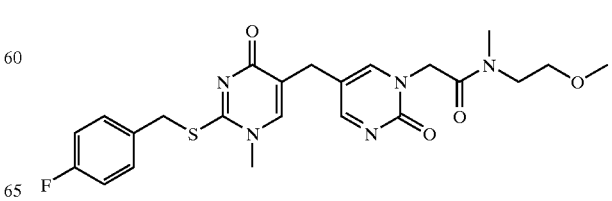

Prepared analogously to example 3. ¹H-NMR (CDCl₃) δ2.98 and 3.17 (3H,2xs), 3.34 and 3.38 (3H,2xs), 3.4–3.7 (9H,s), 4.47 (2H,s), 4.75 and 4.81 (2H,2xs), 6.9–7.1 (2H,m), 7.18 and 7.20 (1H,2xs), 7.3–7.5 (2H,m), 7.7–7.85 (1H,m), 8.49 (1H,bd); MS (APCI+) found (M+23)=510; C₂₃H₂₆FN₅O₄S requires 487.

EXAMPLE 10

1-Methyl-2-(4-fluorobenzyl)thio-5-(1-(N-(naphth-1-ylmethyl)-N-methylaminocarbonylmethyl)-2-oxopyrimid-5-ylmethyl)pyrimidin-4-one

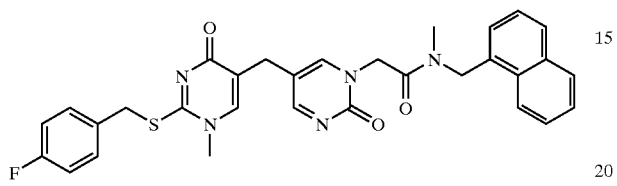

Prepared analogously to example 3. ¹H-NMR (CDCl₃) δ2.99 and 3.12 (3H,2xs), 3.35–3.6 (5H,m), 4.46 and 4.47 (2H,2xs), 4.67 and 4.79 (2H,2xs), 5.07 and 5.17 (2H, 2xs), 6.9–7.1 (2H,m), 7.1–7.7 (7H,m), 7.7–8.05 (4H,m), 8.45–8.6 (1H,m); MS (APCI+) found (M+1)=570; C₃₁H₂₈FN₅O₃S requires 569.

EXAMPLE 11

1-Methyl-2-(4-fluorobenzyl)thio-5-(1-(4-hydroxy-4-benzylpiperidin-1-ylcarbonylmethyl)-2-oxopyrimid-5-ylmethyl)pyrimidin-4-one

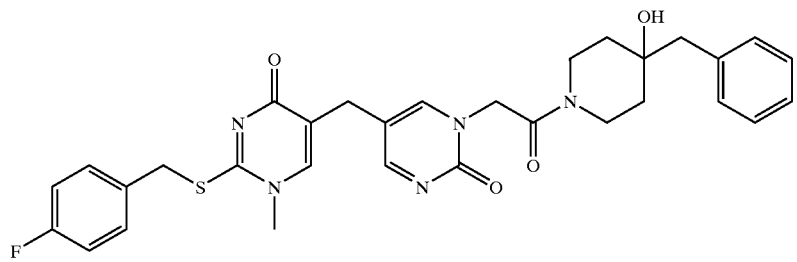

Prepared analogously to example 3. ¹H-NMR (d₆ DMSO) δ1.25–1.65 (4H,m), 2.71 (2H,s), 2.94, (1H,bt), 3.55–3.7 (1H,m), 3.95–4.1 (1H,m), 4.41 (3H,s), 4.65–4.85 (2H,m), 7.05–7.35 (7H,m), 7.4–7.6 (2H,m), 7.71 (1H,s), 7.87 (1H,d), 8.54 (1H,d); MS (APCI+) found (M+1)=590; C₃₁H₃₂FN₅O₄S requires 589.

EXAMPLE 12

1-Methyl-2-(4-fluorobenzyl)thio-5-(1-(N-(1-octyl)-N-methylamino-carbonylmethyl)-2-oxopyrimid-5-ylmethyl)pyrimidin-4-one

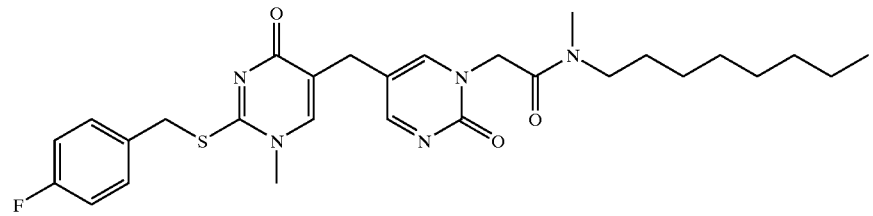

Prepared analogously to example 3. ¹H-NMR (CDCl₃) δ0.8–0.95 (3H,m), 1.10–1.65 (12H,m), 2.95 and 3.09 (3H, 2xs), 3.35 (2H,t), 3.49 (2H,s), 3.52(3H,s), 4.47 (2H,s), 4.74 (2H,s), 6.9–7.1 (2H,m), 7.19 (1H,s), 7.3–7.5 (2H,m), 7.75 (1H,m), 8.48(1H,m); MS (APCI+) found (M+1)=542;

EXAMPLE 13

1-(N-(1-Octyl)-N-methylaminocarbonylmethyl)-2-(4-fluorobenzyl)thio-5-(1-ethoxycarbonylmethyl-2-oxopyrimid-5-ylmethyl)pyrimidin-4-one

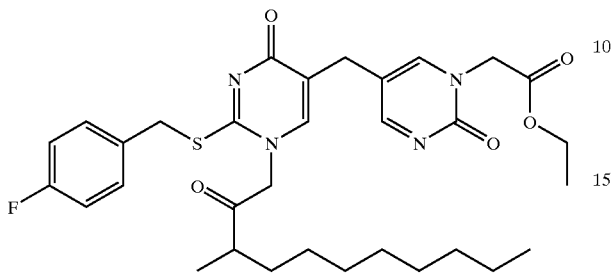

Prepared analogously to example 1. $^1$H-NMR (CDCl$_3$) δ0.8–1.0 (3H,m), 1.15–1.75 (15H,m), 2.94 and 3.00 (3H, 2xs), 3.23 and 3.35 (2H,2xt), 3.47 (2H,s), 4.22 (2H,q), 4.46 (2H,s), 4.57 (2H,s), 4.73 and 4.75 (2H,2xs) 6.9–7.1 (2H,m), 7.35–7.45 (3H,m), 7.87 (1H,m), 8.44 (1H,m); MS (APCI+) found (M+1)=614; C$_{31}$H$_{40}$FN$_5$O$_5$S requires 613.

EXAMPLE 14

1-(N-(1-Octyl)-N-methylaminocarbonylmethyl)-2-(4-fluorobenzyl)thio-5-(1-carboxymethyl-2-oxopyrimid-5-ylmethyl)pyrimidin-4-one

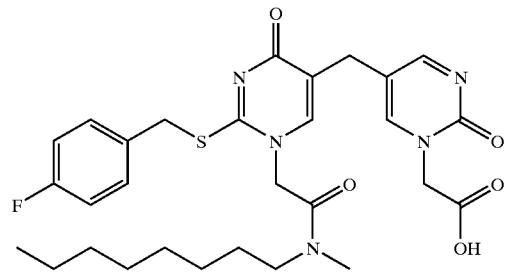

Prepared analogously to example 2 except that acidification was carried out with 10% aqueous NaHSO$_4$ to pH 3, and the crude product after filtration was recrystallised from acetonitrile. $^1$H-NMR (d$_6$ DMSO) δ0.8–0.95 (3H,m), 1.1–1.65 (12H,m), 2.82 and 2.95 (3H,2xs), 4.40 (2H,s), 4.56 (2H,s), 4.84 and 4.85 (2H,2xs), 7.05–7.2 (2H,m), 7.35–7.50 (2H,m), 7.54 and 7.58 (1H,2xs), 8.04 (1H,d), 8.55 (1H,d); MS (APCI−) found (M−1)=584; C$_{29}$H$_{36}$FN$_5$O$_5$S requires 585.

EXAMPLE 15

1-(N-(1-Dodecyl)-N-methylaminocarbonylmethyl)-2-(4-fluorobenzyl)thio-5-(1-ethoxycarbonylmethyl-2-oxopyrimid-5-ylmethyl)pyrimidin-4-one

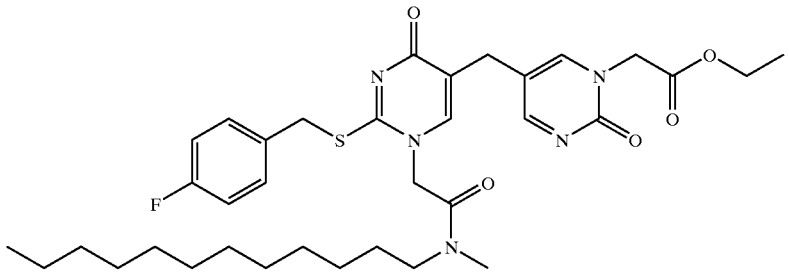

To a stirring solution of intermediate 14 (2.17 g) in dichloromethane (30 ml) was added dropwise with ice cooling a 1M solution of boron tribromide (21.8 ml) such that the temperature remained between 5–10° C. After 4 h the cooling bath was removed and stirring continued for 1.5 h. The mixture was poured on to ice and 0.880 ammonia with stirring, diluted with more dichloromethane, shaken, and the phases allowed to separate slowly. The aqueous phase was further extracted with dichloromethane and the combined extracts dried (MgSO$_4$) and evaporated. The crude material was purified by flash chromatography (fine silica, methanol-ethyl acetate) to give 0.9 g of material that was dissolved in dry dimethylformamide (15 ml) and heated with ethyl bromoacetate (0.17 ml) and anhydrous potassium carbonate (0.43 g) (oil bath 70° C.) with stirring for 2 h. The solvent was evaporated and the residue treated with water and extracted with ethyl acetate. The combined extracts were washed with water, dried (MgSO$_4$), evaporated and purified by flash chromatography (fine silica, methanol-ethyl acetate) to give the title compound as an oil, yield 0.52 g. $^1$H-NMR (CDCl$_3$) δ0.88 (3H, t), 1.25 (21H, m), 1.45–1.75 (2H, m,), 2.95, 3.00 (3H, 2xs), 3.20–3.43 (2H, m), 3.48 (2H, s), 4.23 (2H, q), 4.47 (2H, s), 4.99 (2H, s), 4.66 (2H, m), 7.02 (2H, m), 7.15 and 7.18 (1H, 2xs), 7.37 (2H, m) 7.84 (1H, m), 8.47 (1H, m); MS (APCI+) found (M+1)=670, C$_{35}$H$_{48}$FN$_5$O$_5$S requires 669.

EXAMPLE 16

1-(N-(1-Dodecyl)-N-methylaminocarbonylmethyl)-2-(4-fluorobenzyl)thio-5-(1-carboxymethyl-2-oxopyrimid-5-ylmethyl)pyrimidin-4-one

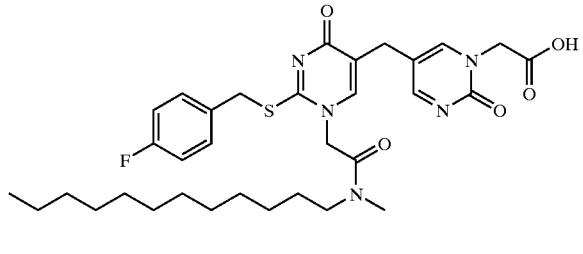

To a stirring solution of 1-(N-(1-dodecyl)-N-methylaminocarbonylmethyl)-2-(4-fluorobenzyl)thio-5-(1-ethoxycarbonylmethyl-2-oxopyrimid-5-ylmethyl)pyrimidin-4-one in 1,4-dioxan (8 ml) was added 0.5M sodium hydroxide (1.56 ml). After 1 h, water (3 ml) was added. After a further hour, the mixture was diluted with water, extracted with ethyl acetate and acidified to pH 3 with aq. sodium bisulphate. The solid which precipitated was filtered, washed with water and ether, heated briefly with acetone and filtered again to give the product as a white solid, yield 0.28 g. $^1$H-NMR (d$_6$-DMSO) δ0.85 (3H, t), 1.22 (18H, m), 1.35–1.61 (2H, m,), 2.78, 2.95 (3H, 2xs), 3.20–3.35 (2H, m), 3.58 (2H, s), 4.40 (2H, s), 4.55 (2H, s), 4.83 (2H, m), 7.10 (2H, m), 7.44 (2H, m), 7.54 and 7.57 (1H, 2xs), 8.03 (1H, m), 8.54 (1H, m) 13.10 (1H, br. s); MS (APCI+) found (M+1)=642, C$_{33}$H$_{44}$FN$_5$O$_5$S requires 641.

EXAMPLE 17

1-(N-(1-Octyl)-N-methylaminocarbonylmethyl)-2-(4-fluorobenzyl)thio-5-(1-(methylaminocarbonylmethyl)-2-oxopyrimid-5-ylmethyl)pyrimidin-4-one

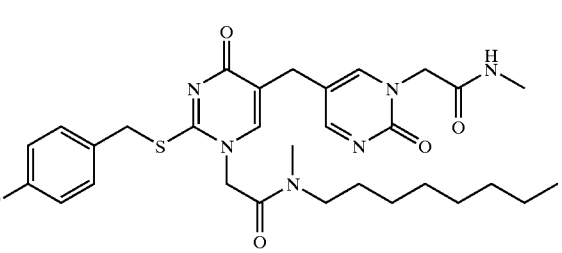

Prepared analogously to example 3. $^1$H-NMR (CDCl$_3$) δ0.8–0.95 (3H,t), 1.1–1.8 (12H,m), 2.73 (3H,bs), 2.93 and 3.00 (3H,2xs), 3.15–3.7 (4H,s), 4.68 (2H,bs), 4.79 (2H, bd), 6.85–7.1 (2H, m), 7.2–7.5 (3H,m), 7.71 (1H,m), 8.63 (1H, bs), 8.82(1H,bs); MS (APCI+) found (M+1)=599; C$_{30}$H$_{39}$FN$_6$O$_4$S requires 598.

EXAMPLE 18

1-(N-(1-Dodecyl)-N-methylaminocarbonylmethyl)-2-(4-fluorobenzyl)-thio-5-(1-(methylaminocarbonylmethyl)-2-oxopyrimid-5-ylmethyl)pyrimidin-4-one

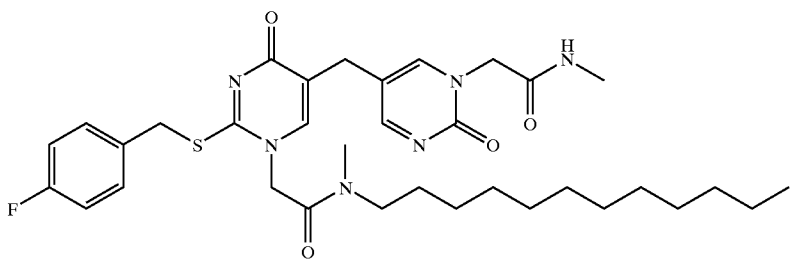

Prepared analogously to example 3. $^1$H-NMR (d$_6$-DMSO) δ0.8–0.95 (3H,m), 1.05–1.7 (20H,m), 2.60 and 2.62 (3H, 2xs), 2.81 and 2.95 (3H,2xs), 3.2–3.55 (4H,m), 4.39 (2H,s), 4.45 (2H,s), 4.84 (2H,bd) 7.05–7.2 (2H,m), 7.35–7.6 (3H, m), 7.98 (1H,d), 8.1–8.25 (1H,m), 8.51 (1H,d); MS (APCI+) found (M+1)=655; C$_{34}$H$_{47}$FN$_6$O$_4$S requires 654.

EXAMPLE 19

1-(N-(1-Dodecyl)-N-methylaminocarbonylmethyl)-2-(4-fluorobenzyl)-thio-5-(1-(1-morpholinocarbonylmethyl)-2-oxopyrimid-5-ylmethyl)pyrimidin4-one

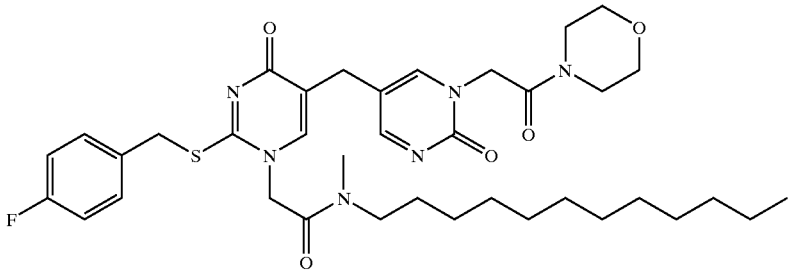

Prepared analogously to example 3. $^1$H-NMR (CDCl$_3$) δ0.8–0.95 (3H,m), 1.05–1.75 (20H,m), 2.6–3.9 (15H,m), 4.45 (2H,bs), 4.55–4.9 (4H,m), 6.85–7.05 (2H,m), 7.1–7.4 (3H,m), 7.87 (1H,bs), 8.47 (1H,s); MS (APCI+) found (M+1)=711; $C_{37}H_{51}FN_6O_5S$ requires 710.

EXAMPLE 20

1-(N-(1-Dodecyl)-N-methylaminocarbonylmethyl)-2-(4-fluorobenzyl)-thio-5-(1-carboxymethyl-2-oxopyrimid-5-ylmethyl)pyrimidin-4-one—sodium salt

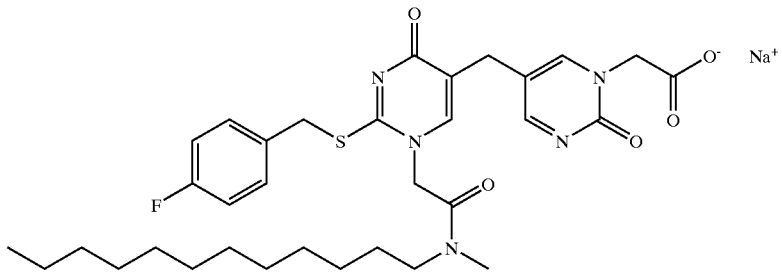

The acid of Example 16 (4.91 g) was added to a solution/suspension of sodium bicarbonate (0.64 g) in water (60 ml). The mixture was stirred at room temperature for 5 min and at 50° C. for 5 min. After sonication for 8 min at room temperature, further water (100 ml) was added and the undissolved material broken up. The mixture was heated and stirred for a further 5 min at 50° C. and sonicated for a further 8 min at room temperature. Any remaining solid was filtered off and washed with water. The clear filtrate was freeze-dried for 16 h to give the sodium salt. $^1$H-NMR (d6-DMSO) δ0.85 (3H,t), 1.1–1.65 (20H,m), 2.81 and 2.94 (3H,2xs), 3.2–3.4 (4H,m), 4.09 (2H,s), 4.40 (2H,s), 4.84 and 4.85 (2H,2xs), 7.05–7.2 (2H,m), 7.4–7.55 (3H,m), 7.87(1H, m), 8.38 (2H,m); MS (ES) found (M+1) (free acid)=642; $C_{33}H_{44}FN_5O_4S$ requires 642.

BIOLOGICAL DATA

1. Screen for Lp-PLA$_2$ Inhibition

Enzyme activity was determined by measuring the rate of turnover of the artificial substrate (A) at 37 C. in 50 mM HEPES (N-2-hydroxyethylpiperazine-N'-2-ethanesulphonic acid) buffer containing 150 mM NaCl, pH 7.4.

(A)

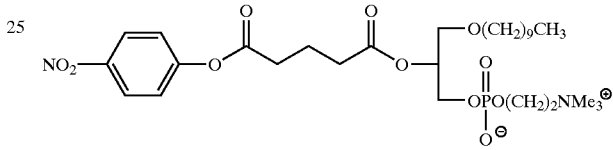

Assays were performed in 96 well titre plates.

Recombinant LpPLA$_2$ was purified to homogeneity from baculovirus infected Sf9 cells, using a zinc chelating column, blue sepharose affinity chromatography and an anion exchange column. Following purification and ultrafiltration, the enzyme was stored at 6 mg/ml at 4° C. Assay plates of compound or vehicle plus buffer were set up using automated robotics to a volume of 170 μl. The reaction was initiated by the addition of 20 μl of 10x substrate (A) to give a final substrate concentration of 20 μM and 10 μl of diluted enzyme to a final 0.2 nM LpPLA$_2$.

The reaction was followed at 405 nm and 37° C. for 20 minutes using a plate reader with automatic mixing. The rate of reaction was measured as the rate of change of absorbance.

RESULTS

The compounds described in Examples 1 to 19 were tested as described above and had respective IC$_{50}$ values of in the range 0.0004 to 3.2 uM.

What is claimed is:

1. A compound of formula (I):

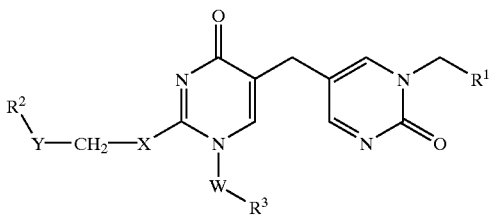

in which:
- $R^1$ is COOH or a salt thereof, $COOR^{10}$, $CONR^{11}R^{12}$, CN or $CH_2OH$;
- $R^2$ is phenyl, naphthyl, pyridyl, pyrimidinyl, pyrazolyl, furanyl, thienyl, thiazolyl, quinolyl, benzothiazolyl, pyridazolyl or pyrazinyl each of which may be unsubstituted or substituted by 1, 2, 3 or 4 substituents selected from $C_{1-4}$alkyl, $C_{1-4}$alkoxy, $C_{1-4}$alkylthio, aryl, aralkyl, hydroxy, oxo, halogen, CN, COOH or a salt thereof, $COO$—$C_{1-6}$alkyl, $CONR^{15}R^{16}$, $NR^{15}COR^{16}$, $SO_2NR^{15}R^{16}$, $NR^{15}SO_2R^{16}$, $NR^{15}R^{16}$, mono to perfluoro $C_{1-4}$alkyl and mono to perfluoro $C_{1-4}$alkoxy;
- $R^3$ is $C_{1-20}$ alkyl, $C_{3-6}$ cycloalkyl, $C_{3-6}$cycloalkyl$C_{1-5}$alkyl, or $C_{1-10}$ alkoxy$C_{1-10}$ alkyl, each of which may be unsubstituted or substituted by 1 or 2 substituents selected from hydroxy, $C_{1-10}$ alkoxy, COOH or a salt thereof, $COOC_{1-15}$ alkyl, $CONR^{17}R^{18}$, $NR^{17}R^{18}$, $NR^{17}COR^{18}$, or $NR^2$, or $R^3$ is $R^2$;
- $R^{10}$ is $C_{1-4}$alkyl or a pharmaceutically acceptable in vivo hydrolysable ester group;
- $R^{11}$ and $R^{12}$ which may be the same or different is each selected from hydrogen, $C_{1-12}$alkyl, $CH_2R^{13}$, $CHR^{14}CO_2H$ or a salt thereof, or $R^{11}$ and $R^{12}$ together with the nitrogen to which they are attached form a 5- to 7 membered ring with or without one further heteroatom which is oxygen, nitrogen or sulphur, and which is unsubstituted or substituted by one or two substituents selected from the group consisting of hydroxy, oxo, $C_{1-4}$alkyl, $C_{1-4}$alkylCO, aryl, and aralkyl;
- $R^{13}$ is COOH or a salt thereof, $COOR^{10}$, $CONR^{11}R^{12}$, CN or $CH_2OH$;
- $R^{14}$ is $CH_2OH$;
- $R^{15}$ and $R^{16}$ are independently hydrogen or $C_{1-4}$ alkyl;
- $R^{17}$ and $R^{18}$ are independently hydrogen, $C_{1-15}$ alkyl, $C_{1-10}$ alkoxy$C_{1-10}$ alkyl or aryl$C_{1-10}$ alkyl;
- W is $SO_2$ or a bond;
- X is O or S; and
- Y is a group of the formula —$A^1$—$A^2$—$A^3$— in which $A^1$ and $A^3$ each represent a bond or a straight chain or branched alkylene group, said alkylene group(s) containing a total of 1 to 10 carbon atoms and $A^2$ represents a bond or O, S, SO, $SO_2$, CO, C=$CH_2$, CONH, NHCO, $CR^{15}R^{16}$, CH=CH or C≡C, providing that when $A^2$ is O, S, SO, $SO_2$ or CONH, $A^3$ contains at least two carbon atoms linking the $A^2$ group and the $CH_2$ group in formula (I).

2. A compound as claimed in claim 1 in which Y is S.

3. A compound as claimed in claim 1 in which W is a bond.

4. A compound as claimed in claim 1 in which $R^2$ is a phenyl ring, which may be unsubstituted or substituted by 4-fluoro.

5. A compound as claimed in claim 1 in which $R^3$ is $C_{1-20}$ alkyl or $R^{17}R^{18}NCOCH_2$— in which $R^{17}$ and $R^{18}$ is each independently $C_{1-15}$ alkyl.

6. A compound as claimed in claim 1 in which $R^1$ is a sodium salt, an ethyl ester, an N-alkyl or di- N-alkyl amide, or an amide in which the N forms part of a 5- to 7 membered ring.

7. A compound of formula (I) as defined in claim 1 selected from the group consisting of:

1-(1-undecyl)-2-(4-fluorobenzyl)thio-5-(1-(ethoxycarbonylmethyl)-2-oxopyrimid-5-ylmethyl)pyrimidin-4-one;

1-(1-undecyl)-2-(4-fluorobenzyl)thio-5-(1-(carboxymethyl)-2-oxopyrimid-5-ylmethyl)pyrimidin-4-one;

1-(1-undecyl)-2-(4-fluorobenzyl)thio-5-(1-(dimethylaminocarbonylmethyl)-2-oxopyrimid-5-ylmethyl)pyrimidin-4-one;

1-methyl-2-(4-fluorobenzyl)thio-5-(1-(ethoxycarbonylmethyl)-2-oxopyrimid-5-ylmethyl)pyrimidin-4-one;

1-methyl-2-(4-fluorobenzyl)thio-5-(1-(carboxymethyl)-2-oxopyrimid-5-ylmethyl)pyrimidin-4-one;

1-methyl-2-(4-fluorobenzyl)thio-5-(1-(1-octylaminocarbonylmethyl)-2-oxopyrimid-5-ylmethyl)pyrimidin-4-one;

1-methyl-2-(4-fluorobenzyl)thio-5-(1-(N-benzyl-N-methylaminocarbonylmethyl)-2-oxopyrimid-5-ylmethyl)pyrimidin-4-one;

1-methyl-2-(4-fluorobenzyl)thio-5-(1-(N-(1-dodecyl)-N-methylaminocarbonylmethyl)-2-oxopyrimid-5-ylmethyl)pyrimidin-4-one;

1-methyl-2-(4-fluorobenzyl)thio-5-(1-(N-(2-methoxyethyl)-N-methylaminocarbonylmethyl)-2-oxopyrimid-5-ylmethyl)pyrimidin-4-one;

1-methyl-2-(4-fluorobenzyl)thio-5-(1-(4-hydroxy-4-benzylpiperidin-1-ylcarbonylmethyl)-2-oxopyrimid-5-ylmethyl)pyrimidin-4-one;

1-methyl-2-(4-fluorobenzyl)thio-5-(1-(N-(1-octyl)-N-methylaminocarbonylmethyl)-2-oxopyrimid-5-ylmethyl)pyrimidin-4-one;

1-(N-(1-octyl)-N-methylaminocarbonylmethyl)-2-(4-fluorobenzyl)thio-5-(1-ethoxycarbonylmethyl-2-oxopyrimid-5-ylmethyl)pyrimidin-4-one;

1-(N-(1-octyl)-N-methylaminocarbonylmethyl)-2-(4-fluorobenzyl)thio-5-(1-carboxymethyl-2-oxopyrimid-5-ylmethyl)pyrimidin-4-one;

1-(N-(1-dodecyl)-N-methylaminocarbonylmethyl)-2-(4-fluorobenzyl)thio-5-(1-ethoxycarbonylmethyl-2-oxopyrimid-5-ylmethyl)pyrimidin-4-one;

1-(N-(1-dodecyl)-N-methylaminocarbonylmethyl)-2-(4-fluorobenzyl)thio-5-(1-carboxymethyl-2-oxopyrimid-5-ylmethyl)pyrimidin-4-one;

1-(N-(1-octyl)-N-methylaminocarbonylmethyl)-2-(4-fluorobenzyl)thio-5-(1-(methylaminocarbonylmethyl)-2-oxopyrimid-5-ylmethyl)pyrimidin-4-one;

1-(N-(1-dodecyl)-N-methylaminocarbonylmethyl)-2-(4-fluorobenzyl)thio-5-(1-(methylaminocarbonylmethyl)-2-oxopyrimid-5-ylmethyl)pyrimidin-4-one;

1-(N-(1-dodecyl)-N-methylaminocarbonylmethyl)-2-(4-fluorobenzyl)thio-5-(1-(1-morpholinocarbonylmethyl)-2-oxopyrimid-5-ylmethyl)pyrimidin-4-one; and 1-(N-(1-dodecyl)-N-methylaminocarbonylmethyl)-2-(4-fluorobenzyl)thio-5-(1-carboxymethyl-2-oxopyrimid-5-ylmethyl)pyrimidin-4-one-sodium salt.

8. A process for the preparation of compounds of formula (I) as defined in claim 1 which comprises reacting a compound of formula (II):

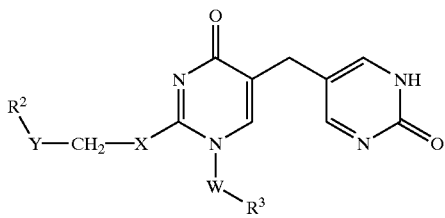

(II)

in which

R$^2$, R$^3$, W, X and Y are as defined in claim 1, with an alkylating agent of formula R$^1$—CH$_2$—L$^1$ in which R$^1$ is as hereinbefore defined and L$^1$ is a leaving group, in the presence of a base; and thereafter, hydrolyzing esters where Z is COOH$^{10}$; or amidating acids where Z is COOH.

9. A pharmaceutical composition comprising a compound of formula (I) as defined in claim 1 and a pharmaceutically acceptable carrier.

10. A method of treating atherosclerosis which comprises administering an effective amount of a compound of formula (I) as claimed in claim 1 to a patient in need thereof.

* * * * *